United States Patent [19]

Place et al.

[11] Patent Number: 4,715,943

[45] Date of Patent: Dec. 29, 1987

[54] APPARATUS FOR SEPARATING A MIXTURE OF COMPONENTS BY THIN LAYER ELECTROPHORESIS

[75] Inventors: John Place, Geneva; André Bregnard, Le Lignon, both of Switzerland

[73] Assignee: Battelle Memorial Institute, Geneva, Switzerland

[21] Appl. No.: 935,591

[22] Filed: Nov. 26, 1986

Related U.S. Application Data

[63] Continuation of Ser. No. 702,721, Feb. 19, 1985, abandoned.

[30] Foreign Application Priority Data

Feb. 22, 1984 [CH] Switzerland .......................... 853/84

[51] Int. Cl.⁴ ............................................. G01N 21/22
[52] U.S. Cl. .............................. 204/299 R; 204/180.6; 204/182.7; 204/182.8
[58] Field of Search ............. 204/299 R, 182.8, 182.7, 204/180.6

[56] References Cited

U.S. PATENT DOCUMENTS

| | | | |
|---|---|---|---|
| 3,432,414 | 3/1969 | Rand | 204/299 R X |
| 3,755,121 | 8/1973 | Schlutz | 204/299 R X |
| 4,199,428 | 4/1980 | Hayashi et al. | 204/299 R |
| 4,332,472 | 1/1982 | Kato | 204/299 R X |
| 4,391,689 | 7/1983 | Golias | 204/299 R |
| 4,515,676 | 5/1985 | Kawai et al. | 204/299 R |
| 4,578,169 | 3/1986 | Vicario et al. | 204/299 R |
| 4,631,120 | 12/1986 | Pohl | 204/299 R |

*Primary Examiner*—Arthur P. Demers
*Attorney, Agent, or Firm*—Cushman, Darby & Cushman

[57] ABSTRACT

This apparatus comprises a magazine (18) of moulds (10) a device (50) for grasping these moulds and allowing each mould to be brought sucessively above a support (30), then above an electrophoretic cell (40). A pipetting device (20, 23) allows each mould placed on the support (30) to be filled with an electrically conductive gel and a mixture of components to be separated by electrophoresis to be introduced thereinto.

Thanks to a device (70) it is possible to decelerate and measure, during electrophoresis, the relative positions of the components of the mixture and their velocity of separation in the gel.

13 Claims, 6 Drawing Figures

APPARATUS FOR SEPARATING A MIXTURE OF COMPONENTS BY THIN LAYER ELECTROPHORESIS

This is a continuation of application Ser. No. 702,721, filed Feb. 19, 1985, which was abandoned upon the filing hereof.

The present invention relates to an electrophoresis apparatus and more especially an apparatus which, in a thin layer medium, permits the separation of a mixture of components capable of being selectively displaced in said medium under the influence of an electrical potential applied thereto, when the medium has been made electrically conducting.

The invention also relates to a mould suitable for said apparatus, and to a process of electrophoresis in which said apparatus and said mould may be used.

It is known that electrophoretic techniques (sometimes also called electrochromatography) as well as the related techniques such as isotachophoresis. Isoelectric focusing and others, consist in subjecting an electrically conductive solution of positively or negatively ionized molecules to an electric field created by two electrodes, an anode and a cathode, so as to cause said (molecules) to migrate in the direction of the electrode of sign opposite to the sign of their own charge. The velocity of electromigration of the charged molecules is connected with certain of their physico-chemical parameters, especially their mass, their charge and their diffusion constant in the medium in question; these make possible the separation of various chemical species according to the particular values of the parameters possessed by these different species. At the end of the process there is obtained a chromatogram (electrophoretogram) in which after development, the various species of molecules thus separated appear in the form of successive zones or spots which are more or less diffuse according to the efficiency of the separation.

From the operational point of view, electrophoretic separation makes it possible either to identify analytically the components of a mixture or, on a larger scale, to purify said components and obtain them in weighable quantity for preparative purposes. In this latter case, it is clear that the electrophoretogram must have a degree of physical stability sufficient to permit one to manipulate it and to isolate the characteristic zones one from another so as to extract from them each of the components which it is desired to obtain.

In the ordinary practice of separating charged organic molecules, such as those of proteins or nucleic acids, it is conventional to use electrophoretic media which comprise gels (agarose, amidon, polyacrylamide, etc) more or less reticulated according to need. Such gels have the property of reducing convection movements in the electrophoretic liquid, and of improving the fractionation of the molecules which are to be separated, as a function of their crosssection and of their obstruction by the mesh units of the network constituted by the gel, and likewise as a function of their surface affinity properties with reference to those of the molecules of the latter.

Gels utilized in electrophoresis are generally prepared by moulding a liquid which is introduced into a plane-faced mould and then left to harden or caused to harden by polymerization. There have recently been described in application U.S. application Ser. No. 656,462 certain techniques for the preparation of such gels, especially for gels in very thin layers, since the use of gels of very small thickness has the effect of improving the separation efficiency on the components of a mixture.

Thus, the gel prepared according to the conventional technique is presented in the form of a thin ribbon or blade of an electrically conductive medium which is rigid or semi-rigid, and at the end (or at some privileged region) of which the sample of the mixture which it is desired to separate is applied, for example by a means of a pipette. This application is often done by way of a special portion of gel ("stacking gel") which allows a preliminary separation of the components to be separated from starting zones which are very thin and accordingly very concentrated in every component, this repartition taking place before the beginning of the electrophoretic migration properly so called.

Elsewhere, in order to perform this (process) according to conventional practice, the edges of the gel are placed in contact with conducting buffer solutions, themselves connected to the poles of a source of electric current by way of appropriate electrodes, the whole (being done in) such manner that the gel is subjected to the desired electric field. The current is then made to circulate in the gel for the desired time, this current and this time being maintained by control means inside well-defined limits. In similar manner the temperature and humidity conditions are maintained, the exact control of these parameters being, in effect, essential for ensuring good working reproducibility.

After the electrophoresis has finished, there follows the chemical fixation of the gel and the analytical components it contains, for example by formaldehyde or trichloroacetic acid, or an appropriate colorant is added which becomes fixed on these components. The gel is then washed free from excess colorant in order to cause the thus marked components to reappear and, at the drying, the electrophoretogram thus developed is subjected to various examinations and measures allowing identification of the separate components and determination of their proportions relative to the original mixture (migration distances, coloration density etc).

In current practice, these different operations and manipulations are carried out separately, and many manufacturers now furnish the various necessary accessories and components for application of electrophoretic techniques in the form of elaborate and sophisticated kits. Thus, U.S. Pat. No. 3,755,121 described a device in the form of a kit for carrying out analysis by electrophoresis. One of the embodiments of this device comprises a disc-shaped receptacle having two annular electrically conducting zones, one central zone and one peripheral zone, connected to one another by "bridges" filled with an electrically conducting gel. This device likewise comprises a cover which is applied to the said receptacle so that, through openings of the cover which coincide with said "bridges" the analytical samples can be introduced, this being done, however, by conventional means, applying a potential to the ends of these "bridges" by way of the said conducting zones.

A scientific article in Analytical Chemistry, Volume 31 (1959), page 825 describes the simultaneous application of centrifugal force and that of electrophoresis. This article actually describes a rotary device which serves as an electrophoretic separation medium (filter paper). This medium being seeded (spotted) in its central zone and an electrical potential being applied to its periphery so that the substances to be separated migrate in the direction of the periphery following a radial trajectory. When the device is set in rotation, the substances being displaced are subjected to a centrifugal gravitational field directed at right angles to this trajectory, so that the latter tends to acquire an inward curve.

Furthermore, British Patent No. 2,073,413 describes a rotary system of "reading" chromatograms or electrophoretograms. This system comprises a disc-shaped rotary plate having disposed in concentric rings a series of chromatograms whose "spots" are successively placed opposite an optical reading device by stepwise rotation of the plate, the reading device carrying an arm for tangential movement with respect to the plate. This device, however, is provided only for effecting the "reading" of the chromatograms and not for carrying them out at the same time.

U.S. Pat. No. 3,927,826 discloses a centrifugal device for preparing pellets which can be used as electrophoresis media in particularly well reproducible conditions. However, the techniques employed in the electophoretic procedures, being part of the prior art, necessitate much experience and skill on the part of the operators.

As a result, efforts are being made at present to develop electrophoretic apparatus which works more or less automatically, and thanks to which the various manipulations described above can be carried out successively without (or with a minimum of) external manual intervention. Thus, the Societe Olympus has recently placed on the market an automatic electrophoresis apparatus for the analysis of blood sera. This apparatus comprises automatic means for successive application of a sample of the serum, that is to say a mixture of polypeptide components which can be separated by electrophoresis, on a membrane consisting of a cellulose acetate gel, means for placing this in contact with a current source and for subjecting it to an electric potential permitting the electrophoretic separation of the components of the sample, means for developing and fixing, by colouration, washing and drying, the electrophoretogram thus obtained, and optical means (a densitometer) for analysing and measuring the latter and thus identifying and determining the concentration of the components in the sample. Thus, the document German Patent No. 30 30 647 describes a device for automatic manipulation of samples in such an automated electrophoresis apparatus.

The present invention accordingly provides apparatus for separating by thin layer electrophoresis a mixture of components capable of being selectively displaced in an electrically conducting medium under the influence of an electric potential applied to the medium, comprising
  (a) means for incorporating said mixture in said medium, the latter consisting of a gel contained in the moulding cavity of a mould for thin layers of polymer:
  (b) means for connecting two distinct portions of this gel to the poles of a current source, characterized by the fact that it additionally comprises
  (c) means for detecting and measuring, during the electrophoresis and/or thereafter, the relative positions of the components of the mixture and their separation velocity in the gel.

The apparatus of the present invention differs from the state of the art mentioned above in particular by the following points: the electrophoretic medium is a thin layer gel (for example a gel of polyacrylamide, of agarose, of gelatine and other collagens or hydrophilic polymers), housed for preference in the cavity of a mould which serves for the moulding of such gels, and, from another aspect, the means for analysing and measuring the electrophoretogram after producing and developing the same, are replaced by means for detecting and measuring the rate of displacement of the components in course of separation as well as, for preference, their optical density in the course of the electrophoretic operation itself and/or after it has been completed.

It will be noted also that, in the present apparatus, there are used for preference gels enclosed in a mould having the appearance of a thin slab of symmetrical form, especially a flat disc, having a central opening and, housed within its thickness and filled with the said gel, one or more elongated compartments or cavitites in channel form, extending radially from this central opening to the periphery of the mould and whose openings, respectively opening above the inside and outside edges of the mould, permit the connection of each of the extremities of the gel to a distinct pole of a source of current by appropriate contact means so as to subject this gel to the said electric potential.

The invention will be better understood with reference to the attached drawings, in which:

FIG. 2b is a section across such a mould along the axis A—A of FIG. 2a;

Figure 1:
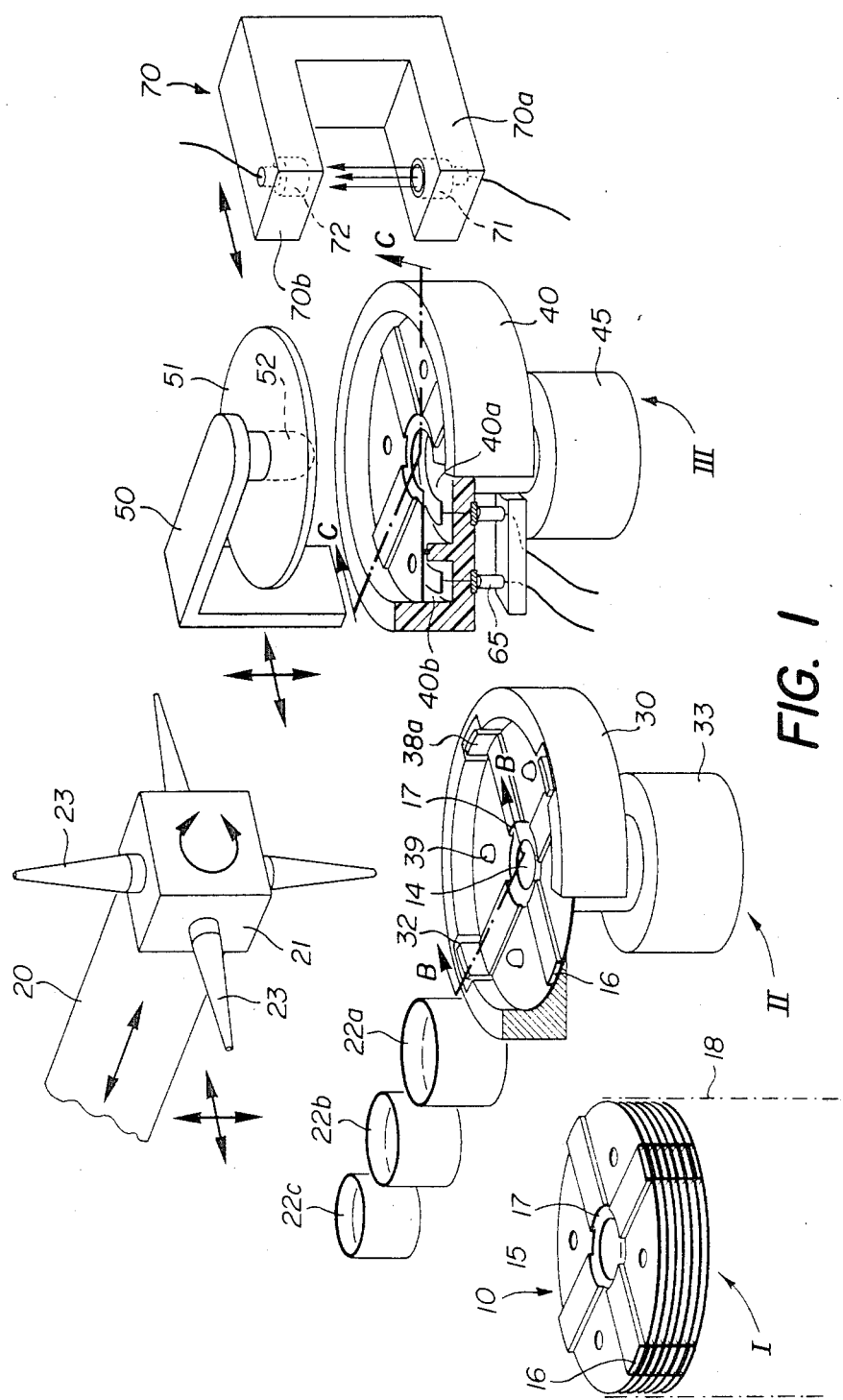
FIG. 1 is a schematic view showing the chief functional features of the electrophoresis apparatus according to the invention.
Figure 2A:
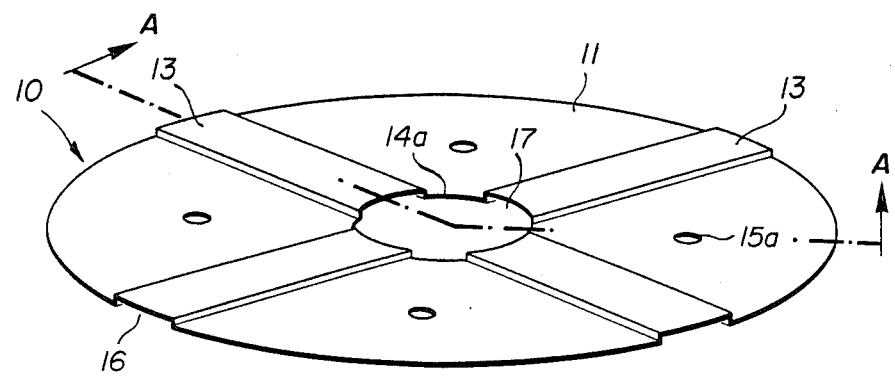
FIG. 2a is a perspective representation of a part of a mould which can be used in the apparatus of FIG. 1.
Figure 2B:
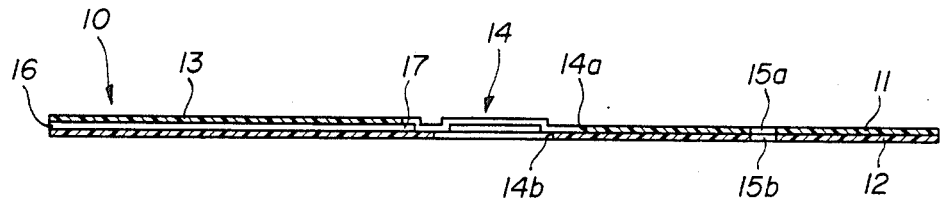
Figure 3:
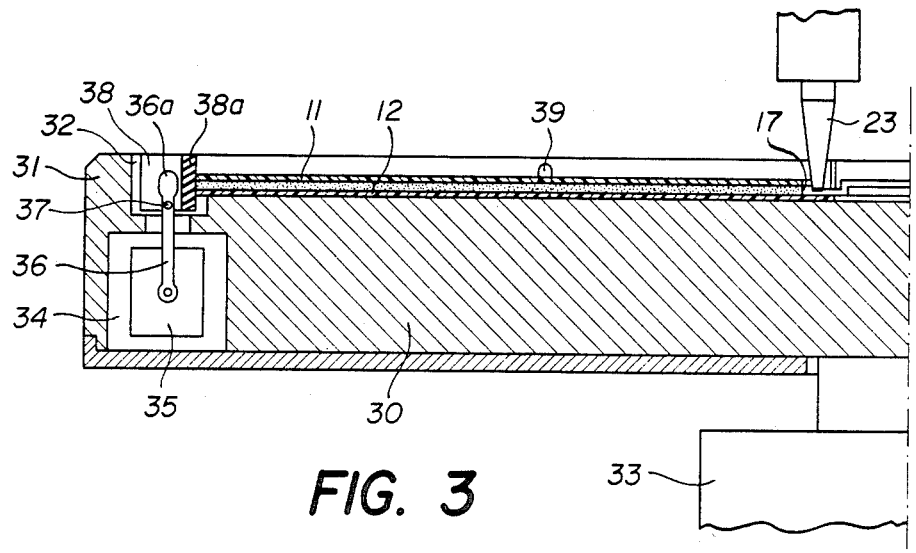
FIG. 3 is a section across the axis B—B of FIG. 1.
Figure 4:
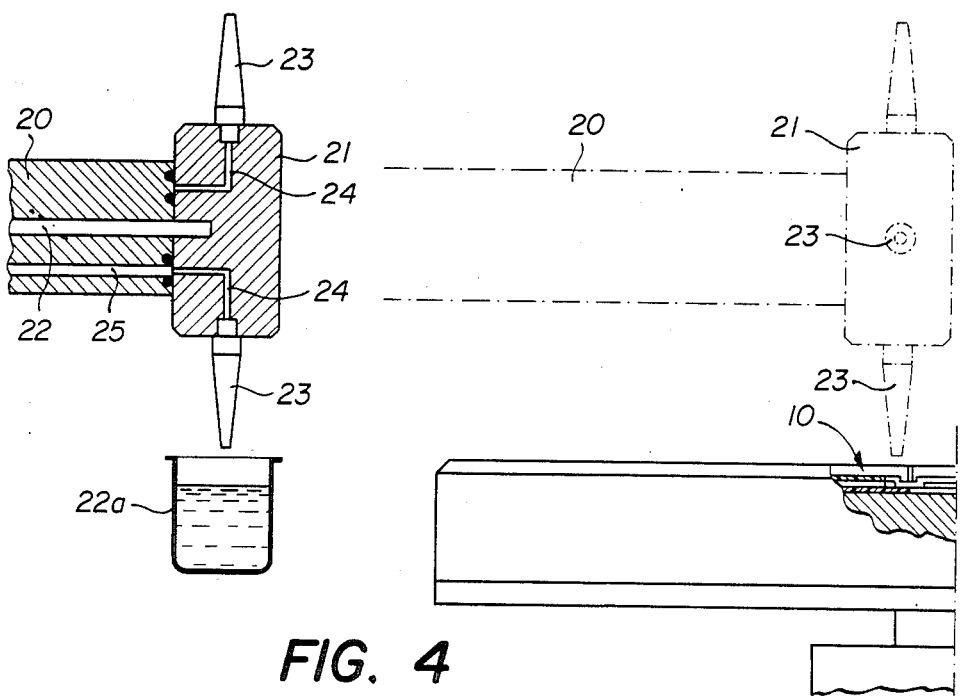
FIG. 4 is an elevation in partial section of a detail of the apparatus of FIG. 1.

The apparatus represented in FIG. 1 comprises, mounted on a base which is not shown, three work posts or positions indicated by the Roman numerals I-III in the drawing. The post I corresponds to a position of storage of the moulds 10, the post II corresponds to a working position wherein the sample, whose components are to be separated, is applied to the gel contained in a mould 10, and the post III corresponds to a working position in which the electrophoresis properly so-called is carried out. It will be noted in passing that position II can equally well correspond to the filling of the mould by a liquid for the production of the gel, since this operation takes place before the application to the gel of the sample for analysis as will be seen further down.

This apparatus comprises a moving arm 20 furnished with a head 21 for dispensing liquid reagents, stored in reservoirs 22a, 22b and 22c, and a transport arm 50 for conveying the discs 10 from one work position to another. In what follows, reference will be made indifferently to FIGS. 2-5.

Each mould 10 (FIG. 2b) is formed by assembly of two superposed discs 11 and 12. The upper disc 11 (FIG. 2a) comprises a sheet of plastics material permeable to UV, moulded so as to form four ridges 13 which can be seen in relief in the drawing. The disc likewise presents a central opening 14a of circular form, and register passages 15a permitting the angular orientation of the mould in its various working positions, as will be seen further on.

The lower disc 12 is flat and presents a central opening 14b, of smaller diameter than that of the opening 14a, and passages 15b disposed to match the passages 15a of the disc 11. These two discs are coaxial and are soldered or adhesively secured one to the other by their outer edges to constitute the mould 10, the space enclosed between the disc 12 and the inner face of the wall which defines the ridges 13 of the disc 11 constituting mould compartments having the form of radial channels with two openings, one, 16, visible at the outer edge of the mould 10, the other 17, on the inner edge of the same.

Of course, other constructions of the mould 10 are also possible: in particular the moulding cavities can be machined out of the thickness of a single slab.

The moulds 10, empty, are stockpiled in the working position I, in a cylindrical dispenser 18, the one which happens to be at the top of the pile being available and capable of being transferred from that position to position II in the course of operation of the apparatus, thanks to a device described hereafter. When the topmost mould of the pile of moulds contained by the dispenser 18 is transferred to the position II, the mould which succeeds it and occupies a position immediately below the latter takes its place and will thus be ready for use when the time comes.

The working position II comprises a circular tray 30 in metal or plastics material, such as aluminium or PVC, is intended to receive a mould 10, and is provided with an annular flange 31 having four equally spaced apart recesses 32 each giving access to a retreat 34 in which is placed (FIG. 3) a device for blocking the opening 16 of each channel of the mould 10 facing a corresponding recess 32, when the mould, entrained by the plate, is set in rotation by a motor 33. As will be seen, this device comprises a fly-weight 35 pivotally mounted on an arm 36 the end 36a of which is pivotally mounted on an axis 37 and supports a shoe 38 to which is fixed a stanching plug 38a specifically designed for blocking the opening 16.

The plate 30 further presents four projections 39, of a diameter substantially corresponding to that of the passages 15a and 15b of the mould 10 and, when the mould has been placed on the plate 30 (FIG. 3), not only permitting it to be fixed in its angular position but also ensuring its rotary entrainment by the plate.

The arm 20 can be displaced by a controlling device, not shown, in the three dimensions of space, ie laterally, from bottom to top and in the axial direction (FIG. 1). This arm 20 comprises an axle 22 (FIG. 4) angularly entrained stepwise by a motor (not shown), at the free end of which (axle) the head 21 is pivotally mounted and carries four pipettes 23 in front, permitting both the uptake and the dispensing of liquids previously aspirated from the reservoirs 22a, 22b or 22c. These pipettes are individually connected, as the angular displacement of the head 21 proceeds, to a conduit 25 connected to means of aspiration and backfeed, not shown, under the control of a general command device of the apparatus, which will be described further down. These means can comprise, for example, one or more pumps adapted to create, at the desired moment, a pressure drop or a pressure enabling a given quantity of liquid to be aspirated into the pipette or to deliver this liquid to a chosen place and at a chosen moment depending on the position of the arm 20 and of the head 21.

The transfer arm 50 is free to move transversely and up and down, as indicated schematically by the arrows appearing at the side of this arm (FIG. 1). It is guided by conventional mechanical elements, not shown, under the control of the general command device of the apparatus, and carries at its free end a disc 51; and an axial tip 52, elastically inflatable and whose outer diameter in the deflated condition is slightly less than that of the central passage 14 which every mould 10 presents. The arm 50 likewise carries means for inflating the elastic tip 52 at will, by effecting a momentary connection between the arm 50 and the mould 10 to be seized, the tip 52 penetrating while deflated into the central passage 14 of the mould and holding the latter in contact with the disc 51 after inflation. It is then easy, by coordinating the displacements of the arm 50 with the inflation and deflation of the tip 52, to seize the mould in one of the working positions I–III of the apparatus, to transfer it and to set it down in another of these working positions.

As a variant, instead of the tip 52, there could be provided a grasping device of a different nature, cooperating with the disc 10, for example a bayonet catch engaging a suitable formation of the hole 14.

Figure 5:
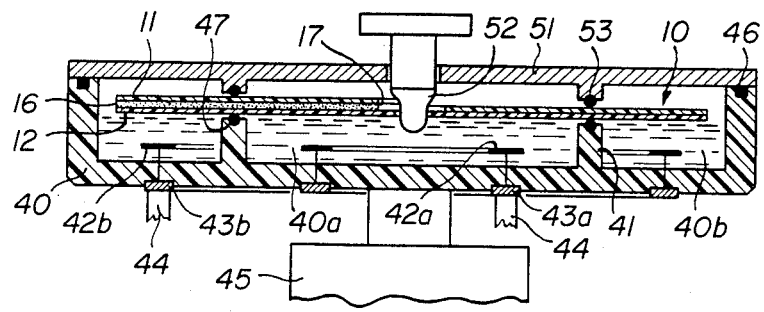
FIG. 5 is a section along the lines C—C of FIG. 1 in a different position of the elements thereof.

The working position III comprises a cylindrical cell 40 of insulating material divided into two coaxial compartments 40a and 40b by an annular partition 41, and containing a buffer electrolyte (FIG. 5). The central compartment 40a encloses an annular electrode 42a electrically connected to an annular collector 43a. Similarly the compartment 40b contains an annular electrode 42b connected to a collector 43b. A sliding electrical contact is assured by carbon (brushes) 44 brushing over the collectors 43a and 43b and collected to distinct poles of a source of electric current, not shown. The cell 40 is kinematically integral with an entrainment motor 45.

The edge of the cell 40 is provided with a circular sealing joint 46 on which the disc 51 of the arm 50 is applied sealingly after the arm 50, under the command of the general control device of the apparatus, deposits a mould 10 in this cell. This disc 51 comprises, housed in a groove in its lower face, an annular seal 53 which presses against the mould 10, whereby the latter is sealed between this joint 53 and another annular joint 47 carried by the partition 41. The compartments 40a and 40b are therefore, by virtue of the presence of the mould 10, sealingly separated one from the other, and the electrolytes which they contain are electrically isolated except for the connection given by the electrophoretic medium contained in the channels of the mould 10, since one end 16 of each channel is in contact with the electrolyte of the compartment 40b and the other end 17 is in contact with the electrolyte of the compartment 40a. It is to be understood, of course, that in this situation, the tip 52 is deflated so as not to interrupt the aforesaid electrical connection between the compartments 40a and 40b.

Figure 6:
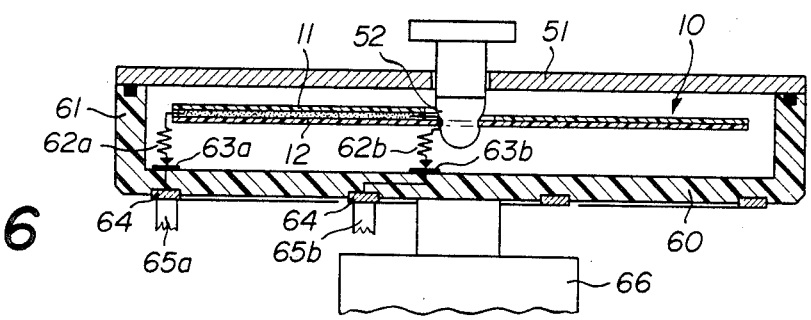
FIG. 6 is a view similar to that of FIG. 5 of a slightly different version.

In the variant of the working device of work position III illustrated in FIG. 6 the latter carries a disc 60 with a flat underside, furnished with a peripheral edge 61 on which the disc 51 is deposited carrying a mould 10 by virtue of the tip 52 in the inflated state, the mould being elastically united with the disc. In this variant, the channels of the mould carry, slotted into their ends 16 and 17, respective pleated metal strips 62a, 62b making brush contact with the annular electrodes 63a and 63b fed with electrical energy, as in the preceding embodiment, by means of brushes or carbons 65a and 65b connected to a source of current, not shown, in contact with the annular collectors 64. The disc 60 is kinematically integral with an entrainment motor 66.

The apparatus described further comprises an electrooptical device or probe intended for observing and measuring, during the course of the electrophoresis, the displacement of each of the components of the mixture being subjected to separation. This device (FIG. 1) exhibits a U-shaped casing 70, one lower arm 70a of which carries a radiation source 71 and an upper arm 70b carries a detector 72. This device 70 can be transversely displaced by means, not shown, governed by the general control device of the machine, for bringing it within range of the cell 40, whereby these arms embrace this cell above and below so that the radiation emitted by the source 71 progressively scans the entire length of a radial channel of the mould 10 subjected to electrophoresis, and that the detector 72 simultaneously recognises a characteristic signal of the reference components. The radiation type is chosen among the wave lengths which are convenient for being absorbed by the components of the mixture subjected to separation. In practice, UV rays are usable but, according to the type of component, other ray types are equally possible: visible light, X-rays and others. In fact, the material of the cell 40, of the mould 10 and of the disc 51 should be permeable to the rays used (a plastics material such as polycarbonate, lucite, PVC or other). The detector 72 gives an electrical rendering of the variations in luminous intensity perceived on the passage of the probe 70 in the form of impulses which are transmitted to the control centre of the apparatus.

The apparatus illustrated includes further control elements for coordinating the movements of the various components described, and for automating the overall function of the machine. Such elements are known per se to the person skilled in the art, who can adapt them and regulate their function to the operative mode chosen from case to case and in view of the type of results sought. These elements include especially a central command and computing unit, for example a microprocessor, attended by conventional peripherals such as a terminal, a visual display unit, programmable or non-programmable memories, a timebase and others, and the necessary interfaces such as amplifying circuits, decoders and integraters of signals furnished by the detector 72, circuits commanding the execution of the various mechanical functions called into play, and a converter of analogue data to digital data etc.

Furthermore, the apparatus can likewise contain position detectors for the various mobile elements for the purpose of controlling and, if necessary, correcting the movement and position of the latter in all the operative phases of the apparatus. The apparatus likewise comprises probes measuring the electrophoretic conditions, that is to say the temperature and the humidity prevailing within the enclosure 40 as well as the electrical conditions (voltage, current intensity) the signals furnished by these probes being likewise transmitted to the central command unit for the purpose of being stored in memory, for display, for control or for automatic correction by feed-back. All these elements are, per se, known to the person skilled in the art and are not shown in the drawings in order to avoid crowding them with details not essential to an understanding of the invention.

All the devices recited can be assembled and made from commercially available components without the need for any particular inventive activity, and can be adapted, according to need, to different types of operations and of chemical components to be studied by electrophoresis.

The manner of operation of the present apparatus will now be indicated by describing the different operating phases in succession.

Before the run starts, the distributor 18 has been charged with a stack of empty moulds 10 and, in their first phase of work the arm 50, piloted by the central control unit, removes a first mould by means of the tip 52 and places it on the plate 30 where it is positioned in the required way by means of the projections 39 penetrating into the passages 15 of the mould. The arm 20 then moves towards the appropriate reservoir 22 (for example 22a) and, acted on by the central command unit, dispenses through a pipette 23 a measured quantity of a monomer (for example a known aqueous solution of acrylamide) this quantity being slowly discharged by the pipette into the opening 17 of each of the four radial channels of this mould, after the arm 20 has been properly placed with respect to the centre 14 of the mould (see FIG. 4). Previously, the plate 30 has been set in rotation by means of the motor 33 at a speed sufficient for the centrifugal force generated to cause the closure of the outer opening 16 of each channel of the mould (by the intervention of the plug 38 pressed by the arm 36a activated by the fly-weight and forces the liquid delivered by the pipette 23 to penetrate radially into the mould cavities so that it accumulates little by little and fills each cavity to a predetermined length. The U.S. application Ser. No. 656,462 has already described the advantages presented by the use of centrifugal force for filling the moulds for gels in thin layers intended for electrophoresis, one of those advantages being the ability to quickly eliminate air bubbles and other discontinuities trapped in the liquid.

When the mould has been filled in the desired manner (generally to about 7/8 or 9/10 of its volume) steps are taken to make its contents gel, whether by waiting the desired length of time if the solution contains the ingredients necessary for hardening, or by irradiation, as described in the U.S. application Ser. No. 656,462.

When the gel has solidified, the sample is then applied by a second one of the pipettes 23 of the head 21, the operative technique being to all intents identical to that of filling the mould, i.e. pumping by the pipette of a measured quantity of mixture to be separated taken from a container 22, for example 22b, addition to the gel, either through the opening 17 as already described, or in the variant by a special opening located in the mould short of the end 17, for example as described in the U.S. application Ser. No. 656,462.

Of course, the apparatus can include reservoirs of liquid additional to the reservoirs 22a, 22b and 22c shown in the drawings, and such additional reservoirs may contain other reagents, samples, or liquids for rinsing the pipettes, for example.

When the sample to be analysed has been incorporated, (the mould having been set in rotation to prevent escape of said sample) the final filling of the mould takes place with a precursor solution of the gel, with the aim of imprisoning the sample. For this there may be used a solution identical to that which provided the main body of the gel, or an independent solution (e.g. stored in a third receptacle 22c), leading to the formation, after setting, of a "stacking" gel mentioned earlier. Of course, if the mould 10 has been specially opened to admit the mixture to be separated, it is unnecessary to introduce a last portion of gel.

It will be noted that, in the present procedure, the various compartments of the mould 10 have been used simultaneously, every one of them having been given the same treatment. An obvious variation is to incorporate samples which differ from one compartment to another. However, it is preferred to proceed as described, since the ability to carry out four identical operations at the same time provides a check on the reproducibility of the procedures.

Once the mould 10 has been filled and the sample for analysis incorporated, the apparatus removes this mould from the plate 30 and automatically brings it into the cell 40 by means of the arm 50, the disc 51, in the role of cover for the cell 40, providing an assurance of the tightness of the cell 40 and the preservation of the chosen conditions for carrying out the electrophoresis.

The latter takes place on command by the central control unit, which automatically regulates the working conditions: the temperature by means of a heating element incorporated in the base of the cell 40 (not shown), and the electrical parameters (voltage and current). These parameters are, of course, read by appropriate sensors of the apparatus and when displayed by a display apparatus which is not shown, comprise part of the useful information transmitted to the operator during the analysis. Since the ends 16 and 17 of the mould cavity are in electrical contact, respectively, with the conducting solutions of the compartments 40a and 40b and the latter are subjected to a potential difference by means of the electrodes 42a and 42b connected to a current source governed by the central control unit, the electrical field is established in the gel of the mould and the components of the sample are displaced within the gel under the influence of the electrophoretic force. During this operation the cell 40 can be maintained stationary or in rotation. In the latter case, the centrifugal force engendered can exercise a special effect on the mode of migration of the various components. In particular it can accelerate or retard the movement of some of the components at the expense of other components or it can compensate for certain disadvantages due to electroendosmosis.

During the performance of the electrophoresis (and of course at its termination) the casing 70 is displaced in a radial tangential movement with reference to the mould so as progressively and systematically to explore the entire field of the mould which has been subjected to electrophoresis. The excitation radiation originating in the source 71 is intercepted, one by one, by the various components being separated (or already separated) and the signal thus detected by the detector 72 is transmitted to the central control unit which treats it electronically and registers and displays the results in the form of data of absorption intensity and velocity of displacement. Thus it is possible at any moment to follow in detail the progress of the electrophoresis by means of the present apparatus, the registered and displayed data giving information as to the nature of the components (their chemical structure in certain cases) and their original concentration in the sample.

I claim:

1. Apparatus for separating by thin layer electrophoresis a mixture of components capable of being selectively displaced in an electrically conducting medium under the influence of an electric potential applied to the medium, comprising (a) means for incorporating said mixture in said medium, the latter consisting of a gel contained in the moulding cavity of a mould for thin layers of polymer;
    (b) means for connecting two distinct portions of this gel to the poles of a current source, characterized by the fact that it additionally comprises
    (c) means for detecting and measuring, during the electrophoresis or, the relative positions of the separated components of the mixture and their separation velocity in the gel.

2. Apparatus according to claim 1, characterized by the fact that the mould has a general disc-like shape, that it has a hole in its center and carries, disposed within its thickness and filled with the said gel, at least one cavity which extends from the centre of the mould to the periphery thereof and the openings of which, opening respectively on the inner and outer edges of the mould, are adapted for connection to said current source so as to establish said electric potential between the ends of the gel.

3. Apparatus according to claims 1 or 2, characterized by the fact that it comprises means for successively transporting the mould from a stockpiled position to a second station of the apparatus where the mixture to be separated is incorporated in the electrophoretic gel, and then to a third station where the electrophoretic separation takes place.

4. Apparatus according to claim 1, characterized by the fact that it additionally comprises means for moulding the gel in situ within the mould, these means including:

i. a motor for setting the mould in rotation;
    ii. a liquid dispenser for introducing a monomer or other liquid precursor of the gel thorugh the central opening of the mould, so that this liquid is displaced and fills the mould under the influence of the centrifugal force due to the rotation, and it is converted into a gel after the mould has been filled.

5. Apparatus according to claim 4, characterized by the fact that said liquid dispenser is likewise provided as means (a) for incorporating in the gel the sample to be separated.

6. Apparatus according to claim 5, characterized by the fact that means (a) comprise an arm which is movable in at least two dimensions of space, equipped with calibrated pipettes and devices for aspirating and delivering a known dose of liquid repetitively.

7. Anparatus according to claim 1, characterized by the fact that the means (b) for connecting the gel to the source of electric current consist of buffered electrolyte solutions which contain two coaxial zones in which the mould is immersed, one said zone being central and the other peripheral to a vat.

8. Apparatus according to claim 1, characterized by the fact that the means (b) comprise metallic strips matched to the section of an opening of the mould cavities and inserted in said openings, these strips being connected to the current source.

9. Apparatus according to claim 1, characterized by the fact that the means (c) are electro-optical and comprise, firstly a source of radiation which is directed at said components subjected to electrophoresis and, secondly, a sensor for this radiation after interaction with said components, the radiation collected by the sensor furnishing desired metrical information in the form of an electric signal.

10. Apparatus according to claim 1, characterized by the fact that a source and a sensor are movable and move with respect to the mould so as to explore the entire field of the gel subjected to electrophoresis.

11. In an automated thin layer electrophoresis apparatus containing a mixture of components in an electrically conductive medium, said components being subject to different rates of relative displacement when placed under the influence of an electric potential, said apparatus comprising,
   (a) holding means for containing said mixture of components in said electrically conductive medium;
   (b) connection means for applying an electric potential across the mixture through said conductive medium; and
   (c) analyzing means for measuring the relative positions of the components, and the separation velocity of the components, in the conductive medium during the application of the electric potential across the conductive medium.

12. Apparatus as in claim 11 wherein said holding means is disk-shaped, the holding means having a cavity therein, said cavity extending from the center of said holding means to the periphery thereof and being filled with said mixture of components in said conductive medium when in use; and wherein the connection means is arranged so as to apply an electric potential across the conductive medium from the center of the holding means at a first end of said cavity to the periphery of the holding means at a second end of said cavity.

13. Automated apparatus for performing thin layer electrophoresis comprising:
   (a) holding means for containing an electrically conductive medium and a sample to be analyzed;
   (b) first transfer means for moving said conductive medium and said sample from storage containers to said holding means when said holding means is at a filling position;
   (c) second transfer means for moving said holding means from a storage position to said filling position, and from said filling position to an electrophoresis separating position;
   (d) connection means for applying an electric potential across said conductive medium while said holding means is in said electrophoresis separating position;
   (e) analyzing means adjacent to said electrophoresis separating position for determining the relative positions of components within said sample and for determining the separation velocity of the components, during electrophoresis.

* * * * *